United States Patent [19]

Fehr et al.

[11] 4,433,183

[45] Feb. 21, 1984

[54] PROCESS FOR THE PREPARATION OF (+)-P-MENTHA-2,8-DIEN-1-OL

[75] Inventors: Charles Fehr, Versoix; Günther Ohloff, Bernex, both of Switzerland

[73] Assignee: Firmenich SA, Geneva, Switzerland

[21] Appl. No.: 366,553

[22] Filed: Apr. 8, 1982

[30] Foreign Application Priority Data

May 4, 1981 [CH] Switzerland .......................... 2875/81

[51] Int. Cl.³ .............................................. C07C 35/14
[52] U.S. Cl. ....................................... 568/829; 568/29; 568/823
[58] Field of Search ........................... 568/823, 829, 29

[56] References Cited

U.S. PATENT DOCUMENTS 4,025,516 5/1977 Razdian et al. .................. 260/345.3

OTHER PUBLICATIONS

House, "Modern Synthetic Reactions," 2nd. ed. W. A. Benjamin Inc., p. 334, (1972).
Razdian "J. Amer. Chem. Soc.", vol. 96, (1974), pp. 5860–5865.
Bowen "Chemical Abstracts", vol. 85, (1976), p. 19027r.
Newhall "J. Organic Chem.", vol. 22 (1958), pp. 1274–1276.
Fisher Reprint from Oct. 1965, "The Citrus Industry Magazine".

*Primary Examiner*—Werren B. Lone
*Attorney, Agent, or Firm*—Pennie & Edmonds

[57] ABSTRACT

Multistep process for preparing (+)-p-mentha-2,8-dien-1-ol from (+)-(R)-limonene. New compounds useful as intermediates in said process.

4 Claims, No Drawings

PROCESS FOR THE PREPARATION OF (+)-P-MENTHA-2,8-DIEN-1-OL

BRIEF SUMMARY OF THE INVENTION

Process for preparing (+)-(1S,4R)-p-mentha-2,8-dien-1-ol, which comprises
(a) epoxidizing (+)-(R)-limonene to yield a diastereomeric mixture of (+)-(1R,2S,4R)-1,2-epoxy-8-p-menthene and (+)-(1S, 2R, 4R)-1,2-epoxy-8-p-menthene;
(b) treating the above mixture with thiophenol to yield (+)-(1S, 2S, 4R)-2-phenylthio-8-p-menthen-1-ol after separation thereof from unreacted (+)-(1R,2S,4R)-1,2-epoxy-8-p-methene;
(c) oxidizing the thus obtained 2-phenylthio-8-p-methene into the corresponding sulfoxide, and
(d) heating (1S, 2S, 4R)-1-hydroxy-8-p-menthen-2-phenylsulfoxide of step (c) at a temperature comprised between about 400° and 450° C.

BACKGROUND OF THE INVENTION (−)-Δ⁹-Tetrahydrocannabinol, one of the physiologically active components of cannabis, has recently encountered a renewed interest in the art, especially in view of the possibility of its therapeutical applications. Many of the processes for its preparation make use of (+)-p-mentha-2,8-dien-1-ol as an intermediate [J. Amer. Chem. Soc. 96, 5860 (1974); U.S. Pat. No. 4,025,516 and Helv. Chim. Acta 52, 1102 (1969) for example] which can be prepared from limonene via its oxidation with singlet oxygen or via an enzymatic reaction [see Ann. Chem. 674, 93 (1964) and Chem. Abstr. 85, 19027 (1976), respectively].

The present invention has the advantage to provide a new and original synthetic process for the preparation of (+)-p-mentha-2,8-dien-1-ol in a small number of reaction steps by making use of cheap and easily available reactants, thus rendering the whole synthesis commercially more attractive.

PREFERRED EMBODIMENTS OF THE INVENTION

The originality of the process of the present invention essentially lies in the particular reaction sequence used as well as in the particular choice of the reactants. The process can be visualized as follows:

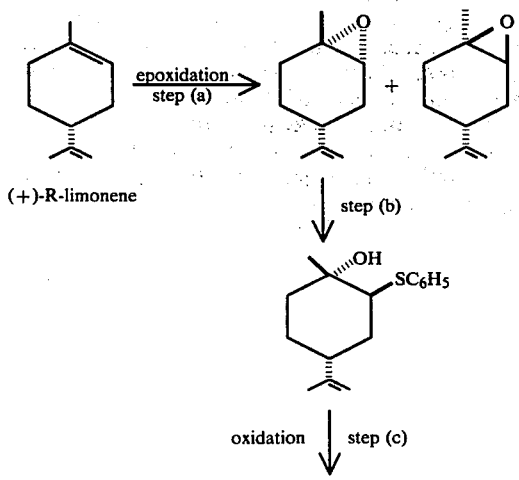

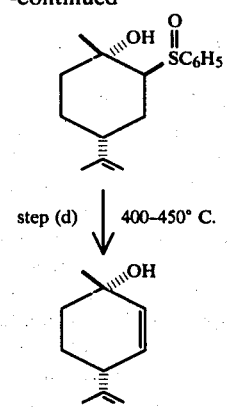

C₆H₅ = phenyl
(+)-(1S,4R)-p-mentha-2,8-dien-1-ol

Reaction step (a) consists in epoxidizing the endocyclic double bond of limonene: this can be effected by means of an organic peracid, preferably in the presence of an inert organic solvent. To this end, one can advantageously use peracetic acid in a chlorinated hydrocarbon such as e.g. dichloromethane, dichloroethane or trichloroethane, optionally in the presence of a basic agent, sodium carbonate for example.

The said epoxidation yields a 1:1 diastereomeric mixture of (+)-1S,2R,4R)-1,2-epoxy-8-p-menthene and (+)-(1R,2S,4R)-1,2-epoxy-8-p-menthene.

Separation of each diastereomer from that mixture is not necessary, in fact the subsequent treatment with thiophenol is more conveniently effected with the obtained diastereomeric mixture. Whenever required, unreacted (+)-(1R,2S,4R)-1,2-epoxy-8-p-menthene can be isolated from the reaction mixture of step (b) or even in a further reaction step; we noted, however, that its presence did not negatively influence the course of the overall process.

The treatment of limonene-epoxides with thiophenol is effected in the presence of an inert organic solvent, optionally in admixture with a polar cosolvent such as dimethyl formamide for example. The said treatment, moreover, is carried out in the presence of stoechiometric amounts of sodium or potassium carbonate. The said reaction, which is preferably effected at a temperature near to the boiling point of the selected solvent or mixture of solvents yields the desired (+)-(1S,2S,4R)-2-phenylthio-8-p-menthen-1-ol in good yields.

The thus obtained compound is then oxidized into the corresponding sulfoxide, preferably by means of hydrogen peroxide, and the resulting reaction product is heated finally to give the desired (+)-(1S,4R)-p-mentha-2,8-dien-1-ol.

Though the thermal treatment can be effected at temperatures varying within wide limits, we could establish that temperatures of between about 400° and 450° C. are those which enable to achieve the best yields.

The following example is deemed to illustrate the present invention in a more detailed manner; however, it has not to be considered as a limitation thereof. In said example, the temperatures are given in degrees centigrade and the abbreviations possess the sense common in the art.

EXAMPLE

(a) (+)-(1R,2S,4R)-1,2-epoxy-8-p-menthene and (+)-(1S,2R,4R)-1,2-epoxy-8-p-menthene 480 g (2.5 M) of 40% peracetic acid in acetic acid were added dropwise, over a period of 2 hours, to a cold (0°) suspension of 272 g (2 M) of (+)-(R)-limonene and 106 g (1 M) of sodium carbonate in 800 ml of trichloroethane, under good stirring. The reaction temperature was kept at 0° to 5° during the addition, then at 0° for 2 further hours. After successive washing with water (1 l), a 5% aqueous solution of $Na_2SO_3$ (1 l), and a 10% aqueous solution of sodium bicarbonate, (1 ), drying over sodium sulfate and final evaporation at 85°/740 Torr, there was obtained a crude material which gave, after distillation, 263.8 g (81% yield) of a 1:1 diastereomeric mixture of the title compounds (93% purity); b. p. 70°–85°/15 Torr.

(b) (+)-(1S,2S,4R)-2-phenylthio-8-p-menthen-1-ol

A suspension of 164 g (1 M) of the above diastereomeric mixture, 83 g of potassium carbonate and 60.5 g (0.556 M) of thiophenol in a mixture of 380 ml of toluene and 20 ml of dimethylformamide was heated under reflux for 10 hours. After cooling to room temperature and addition of water, the separated organic layer was successively washed with water and with brine, dried over sodium sulfate and evaporated. After distillation in a bulb apparatus, the desired thioether (131 g; ca. 100% yield) was separated from unreacted (+)-(1R,2S,4R)-1,2-epoxy-8-p-menthene. The title compound thus prepared was characterized as follows:

$[\alpha]^{20}_D$(CHCl_3, 1.55%)= +96.8°;

IR (CDCl_3): 3610, 3450, 3075, 2940, 1640, 1585, 1480, 1440, 1380 cm$^{-1}$;

NMR (60 MHz): 1.40 (3H, s); 1.50–1.90 (9H, m); 2.08 (1H, dxdxd, J≈13.9 and 3.5); 2.37 (1H, m); 3.31 (1H, t, J≈4); 4.68 (2H, s); 7.16–7.51 (5H, m) δ ppm;

MS: M+ =262(1); m/e: 220(8), 152(17), 137(18), 123(68), 109(86), 95(32), 83(35), 67(61), 55(45), 43(100).

(c) (1S,2S,4R)-1-hydroxy-8-p-menthen-2-phenylsulfoxide 450 g (7.5 M) of acetic acid followed by a portion of 38 g (0.75 M) of 70% hydrogen peroxide were added to a cold (0°) solution of 131 g (0.5 M) of the thioether of step (b), under good stirring. The reaction mixture was further stirred for 15 hours at 0° to 5° then successively washed with water, a 5% aqueous solution of $Na_2SO_3$ and a 10% solution of sodium bicarbonate, dried over sodium sulfate and finally concentrated under reduced pressure (0.1 to 10 Torr) to afford 142 g (0.5 M) of the desired sulfoxide. An analytical sample was purified by column chromatography (silica gel—eluent: 4:1 mixture of cyclohexane and ethyl acetate). The two diastereomers thus obtained were further separated each from the other by crystallization and filtration.

diasteromer a: m.p.: 149°–152° $[\alpha]^{20}_D$ (CHCl_3, 0.58%)= +25.9°;

IR (CDCl_3): 3600, 3380, 2940, 1440 and 1135 cm$^{-1}$.

NMR (60 MHz): 1.45 (3H, s); ca. 1.50–2.05 (10H, m); 2.36–2.63 (1H, t, J≈6.5); 4.25 (1H, s); 4.64 (1H, broad s); 7.38–7.62 (5H, m) δ ppm.

diastereomer b:

$[\alpha]^{20}_D$ (CDCl_3, 0.93%)= –108.6°;

IR (CDCl_3): 3410, 3090, 1640, 1425, 1380, 1130 and 1005 cm$^{-1}$;

NMR (60 MHz): 1.35 (3H, s); ca. 1.35–2.05 (9H, m); 2.27 (1H, m); 3.10 (1H, dxd, J≈8 and 9); 4.08 (1H, s); 4.46 (1H, broad s); 5.33 (1H, s); 7.32–7.80 (5H, m) δ ppm.

(d) (+)-(1S,4R)-p-mentha-2,8-dien-1-ol

A solution of 10 g of the crude material of step (c) in a mixture of 10 g of piperidine and 10 g of toluene was passed through a quartz column (3.50 m long) heated at 425° and kept under reduced pressure (20 Torr); the introduction of the solution was effected by means of an iron needle (15 cm long). The resulting reaction mixture was collected at −70° then successively washed with water and brine and finally dried over sodium sulfate. After evaporation and distillation of the crude residue on a VIGREUX column (10 cm long), there were obtained 3.4 g of the desired product having b. p. 65°–75°/2 Torr. The thus prepared compound was found identical with an analytical sample obtained in accordance with a prior described method.

What we claim is:

1. Process for preparing (+)-(1S,4R)-p-mentha-2,8-dien-1-ol, which comprises
   (a) epoxidizing (+)-(R)-limonene to yield a diastereomeric mixture of (+)-(1R,2S,4R)-1,2-epoxy-8-p-methene and (+)-1S,2R,4R)-1,2-epoxy-8-p-methene by means of an organic peracid;
   (b) treating the above mixture with thiophenol in an inert organic solvent in the presence of sodium or potassium carbonate at a temperature near the boiling point of the selected solvent or mixture of solvents to yield (+)-(1S,2S,4R)-2-phenylthio-8-p-methene-1-ol after separation thereof from unreacted (+)-(1R,2S,4R)-1,2-epoxy-8-p-menthene;
   (c) oxidizing the thus obtained 2-phenylthio-8-menthene into the corresponding sulfoxide, and
   (d) heating (1S,2S,4R)-1-hydroxy-8-p-menthene-2-phenylsulfoxide of step (c) at a temperature comprised between about 400° C. and 450° C.

2. Process according to claim 1, which comprises epoxidizing (+)-(R)-limonene with peracetic acid.

3. Process according to claim 1, which comprises heating (1S,2S,4R)-1-hydroxy-8-p-menthen-2-phenylsulfoxide in the presence of toluene and at a pressure higher than the atmospheric pressure.

4. Process according to claim 1, which comprises treating the mixture of step (b) with the organic solvent and a polar co-solvent.

* * * * *